United States Patent
Gluderer

(10) Patent No.: US 7,455,686 B2
(45) Date of Patent: Nov. 25, 2008

(54) DEVICE FOR DELIVERING CHEMICAL/PHYSICAL PARAMETERS AND ASSOCIATED CONTROL DEVICE

(76) Inventor: Lothar Gluderer, Freundsberg 38, A-6130 Schwaz (AT)

(*) Notice: Subject to any disclaimer, the term of this patent is extended or adjusted under 35 U.S.C. 154(b) by 0 days.

(21) Appl. No.: 10/629,926

(22) Filed: Jul. 30, 2003

(65) Prior Publication Data
US 2004/0049252 A1 Mar. 11, 2004

Related U.S. Application Data

(63) Continuation of application No. PCT/AT02/00013, filed on Jan. 16, 2002.

(30) Foreign Application Priority Data

Jan. 30, 2001 (AT) ............................. A 149/2001

(51) Int. Cl.
*A61F 7/00* (2006.01)
(52) U.S. Cl. ........................................ 607/104; 607/108
(58) Field of Classification Search .................. 607/96, 607/104, 108–112
See application file for complete search history.

(56) References Cited

U.S. PATENT DOCUMENTS

| | | | |
|---|---|---|---|
| 4,338,944 A * | 7/1982 | Arkans | 607/104 |
| 4,667,672 A | 5/1987 | Romanowski | |
| 5,411,494 A | 5/1995 | Rodriguez | |
| 5,411,541 A * | 5/1995 | Bell et al. | 607/104 |
| 5,941,907 A | 8/1999 | Augustine | |
| 5,989,285 A * | 11/1999 | DeVilbiss et al. | 607/107 |
| 6,443,164 B1 * | 9/2002 | Parker et al. | 132/333 |
| 6,497,720 B1 * | 12/2002 | Augustine et al. | 607/96 |
| 6,623,511 B1 * | 9/2003 | Daffer et al. | 607/82 |
| 6,685,731 B2 * | 2/2004 | Kushnir et al. | 607/104 |

FOREIGN PATENT DOCUMENTS

| | | |
|---|---|---|
| CA | 2 276 471 A1 | 7/1998 |
| EP | 0 144 571 A1 | 6/1985 |
| EP | 1 002 510 A1 | 5/2000 |
| WO | 99/44552 | 9/1999 |
| WO | 00/23144 | 4/2000 |
| WO | 00/67685 | 11/2000 |
| WO | 02/078584 A1 | 10/2002 |

* cited by examiner

*Primary Examiner*—Roy D Gibson
(74) *Attorney, Agent, or Firm*—Laurence A. Greenberg; Werner H. Stemer; Ralph E. Locher

(57) ABSTRACT

A device for application to a body or body parts and releasing chemical/physical parameters has an applicator with at least two layers. A space formed between the layers includes at least one chamber and/or one channel for releasing the chemical/physical parameters that can be filled with fluidic, i.e., gaseous and/or liquid, media. A control device is connected for controlling parameters such as flowthrough volume, temperature, pressure, and the like, of the media in the chambers or channels. Biosensors for detecting body parameters such as temperature, EKG, and the like are connected to the control device.

22 Claims, 3 Drawing Sheets

FIG.3A 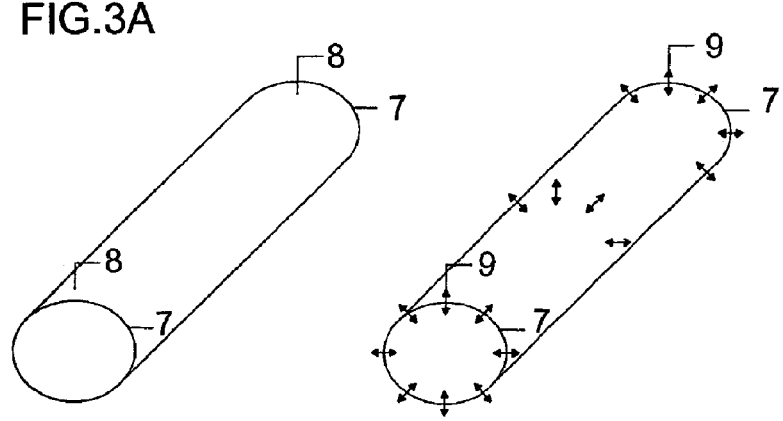 FIG.3B
FIG.3C 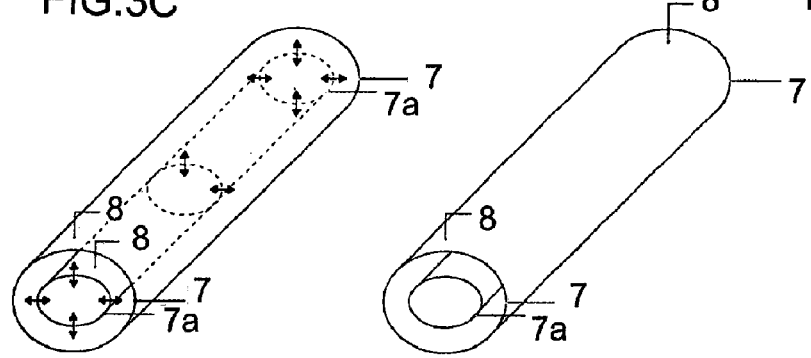 FIG.3D

DEVICE FOR DELIVERING CHEMICAL/PHYSICAL PARAMETERS AND ASSOCIATED CONTROL DEVICE

CROSS-REFERENCE TO RELATED APPLICATION

This application is a continuation of copending International Application No. PCT/AT02/00013, filed Jan. 16, 2002, which designated the United States and which was not published in English.

BACKGROUND OF THE INVENTION

Field of the Invention

The invention relates to a device for application on a human body or parts thereof and for releasing chemical/physical parameters.

External therapeutic applications such as thermal packs, cold packs, mud packs, Thalasso baths, and hay baths are among the most popular forms of treatment today and are widely used in a multitude of facilities such as hospitals, rehabilitation centers, spas, and the like. Improvements of these therapies are therefore sought. Particularly in the area of local applications such as those represented by packs, more cost-effective and simpler devices could be made available which are more effective and easier to apply and which achieve an improved therapeutic or comfort effect.

One such improvement has been known heretofore from European patent EP 144 571. There, there is disclosed a device for applying heat packs. These can be placed in contact with an adjoining heat accumulator or heat reservoir, whereby heat packs are applied to the parts of the body requiring treatment and provided with an isolating layer that blocks the heat transmission. It is then fastened by means of a compress film that is under pressure, this being chargeable with pressure by means of a heatable or heated liquid, slurry, or gaseous medium that serves as the heat reservoir. This type of compress film serves not only for the secure application of the heat packs and the isolating layer but also as a heat supply by means of the medium in the compress film, which is heatable as well as circulatable.

The compress film can be disposed on the top side of a tub under tension such that they can be raised or lowered, whereby heatable medium can be introduced into the tub itself (or in a balloon in the tub) and serves directly or indirectly as a heat supply. The balloons can also act as a compress film on the patients that are immersed in the tub. The balloon can be subdivided so that there emerge side balloons, among others, which can be further subdivided by additional internal separating walls into sectors that are separately passed by the heating medium. Circulation and heating of the balloons and/or the side balloons is achieved by inflow and outflow via a heat exchanger or via a heater and a pump. The balloon may also be connected to the side balloons by a backflow line with a backflow throttle valve.

In any event, in order to achieve a proper and goal-oriented heat therapy by means of that device, several individual films or layers must be successively applied at or on the body or body part requiring treatment. For this reason, simple and rapid pack application can be achieved only with difficulty, which is often disadvantageous for the patient, who has to spend a longer time in an uncomfortable position or posture. Furthermore, a direct application of the treatment medium, such as mud, sludge, or the like, through the heat packs that are applied to the body parts is possible, but these heat packs cannot be dosed or controlled. Besides this, only heat packs in the sense of solid or viscous substances such as mud or sludge can be utilized. A direct release of liquid or gaseous media is not possible.

A further disadvantage of that device emerges with the application of pressure and/or temperature, which can be done without complications but which can be controlled only to a limited extent. This means that an assistant or a doctor must perform this control, and therefore the pressure and temperature behavior cannot be optimally adapted to the needs of the patient, who herself has neither a passive nor an active influence on the pressure and temperature.

SUMMARY OF THE INVENTION

It is accordingly an object of the invention to provide a device for the therapeutic application on a human body or parts thereof and a control system which overcomes the above-mentioned disadvantages of the heretofore-known devices and methods of this general type and which enables a one-time placement of an applicator without additional application aids, and to provide an additional emission such as steam, vapor, moisture, or the like.

With the foregoing and other objects in view there is provided, in accordance with the invention, a device for releasing chemical/physical parameters and for applying to bodies or body parts. The device comprising:

an applicator having at least two layers defining a space therebetween with at least two chambers or channels configured to be individually and independently fillable with fluidic media (gaseous and/or liquid) for releasing the chemical/physical parameters; a control device connected to the applicator for controlling functional parameters, including a flow volume, a temperature, and a pressure, of the medium in the space; and sensors (e.g., bio sensors) connected to the control device, whereby respective the chambers or channels are controlled by the control device in dependence on the body parameters detected by the sensors.

The inventive device of the type described above is wherein the device comprises an applicator with at least two layers, and the space between the layers includes at least one chamber and/or channel for discharging chemical/physical parameters that can be filled with gaseous and/or liquid media, and that the device further comprises at least one control device for controlling parameters such as flow volume, temperature, or pressure of the media in the chamber(s) or channels, whereby biosensors for detecting body parameters such as temperature or EKG are connected to the control device.

The invention realizes not only an indirect release of chemical/physical parameters realized but also a simultaneous pressure charging which holds the applicator in direct contact to the body. The chemical/physical parameters encompass the emission of gaseous and/or liquid media as well as pressure, temperature, steam, fluid such as water containing essences or scents (aromatherapy), or viscous substances.

The space between the layers is advantageously subdivided into at least two chambers and/or channels for outputting the chemical/physical parameters, which are fillable with gaseous and/or liquid media. Through the at least two chambers and/or channels that are fillable with such media, one of these media by itself or two of these media in mixed form, or possible intermediate stages thereof, can be discharged onto the body that is being treated. The at least two chambers/channels between the layers also make it possible to perform a release at locally different body parts depending on the position of the applicator or the chambers and/or channels on the body. This release, which implicitly also includes the pressure-charging of the applicator against the body, is additionally controlled by the control device. The control device comprises not only a device by means of which it is possible to control media that are located in the chambers and/or channels (for instance flow volume or temperature) but also suitable devices of a commercial variety that release, condition, mix, and measure such media, and so on, and which can be guided to the chambers and/or channels in a form that is suited to the body. Among other devices, there are provided pressure receptacles for respective gaseous or liquid media, mixing chambers for setting various parameters of the liquid and/or gaseous media like temperature, moisture level, composition of the media, mix ratio, ionization level, etc., pumps, backflow receptacles with filtering devices for reconditioning the media in the chambers/channels, gas dehumidification receptacles for reconditioning reusable gases, nozzle pumps, compressors, fans, warm and cold exchangers, ultrasound humidifiers or bubblers, jets, sensors, or meters such as hygrometers, ionization meters, thermostats and the like, various terminals, valves, and intake and outlet lines for these. The receptacles or chambers with their corresponding equipment such as lines are preferably autonomous, so that the wanted medium can be inserted in each receptacle separately, and unwanted reactions or interactions between individual media are prevented.

It is possible to imagine the following processes in the control devices: A defined amount of liquid, for instance distilled water, is fed to a mixing chamber from a supply receptacle which is filled with the liquid, in order for the liquid to be charged with $O_2$, $CO_2$, $O_3$, or gas mixtures, scents or salts. This media mixture is heated, cooled, or otherwise treated or conditioned during a conduction and ultimately transported to the chambers and/or channels in order to be released onto the body. Of course, alternative processes are also possible which provide a passage or circulation and a subsequent corresponding circulating or reconditioning of the media, for instance a filtering or other purification of the substances, for the purpose of feeding back into the supply receptacles or into the chambers/channels.

For such processes and process combinations of the gaseous and/or liquid media, suitable—and, as already mentioned, commercially available and proven—devices must be provided in simple and/or combined form. In any case, it must be guaranteed that none of the processes for releasing the chemical/physical parameters onto the body can given rise to adverse events, so that a reliable, faultless handling of the inventive device is enabled.

According to the invention, a monitoring and modification of the media that will be released onto the body and that presently sit in the chambers and/or channels can also be influenced by the body itself by means of the biosensors. As mentioned above, these serve for detecting body-specific parameters such as skin temperature and resistance, EKG, EEG, or the like, which are sent to the control device. Such sensors include suitable measuring devices such as thermometers, specific concentration meters, electrical leakage meters, and so on, which derive from the body various temperatures such as core temperatures, peripheral temperatures, various surface temperatures, and so on, electrical resistances, vital values of organisms such as EEG, EKG, and suchlike. The control device can execute modifications of the parameters such as temperature, pressure, flowthrough volume, concentration, composition, or suchlike of the gaseous and/or liquid media based on the body-specific measurement values. This is aided by a computer which is connected to the control device and the biosensors and which processes the measurement values determined by the biosensors and sends them to the control device in a suitable form. It is imaginable that a processing of the measurement values can occur in the computer in that minimum and maximum values or complete sequence grids, for instance of a temperature curve, are stored in computer programs in the computer. It is also imaginable that these computer programs allow simple or more complex sequences of the gaseous or liquid media and associated processes, for instance a pressure curve of the gases that are supplied to the chambers/channels in order to generate a pressure of the applicator on the body which varies within a predetermined range, or a specific dose of a substance into a liquid about to be released onto the body or parallel operations, for instance a fill gas pressure that rises constantly until reaching a maximum value while vapors that are charged with active substances are simultaneously released in defined concentrations. This information—i.e. the sequences which are stored in the computer—is forwarded to the corresponding devices of the control unit, which executes the requested operations. In a simple embodiment, the values that are stored in the computer are compared to the measurement values of the body that are registered by the biosensors, and an adjusted value, for instance a specified temperature, is sent to the control device, so that corresponding modifications or deviations of the parameters of the liquid and/or gaseous media, such as a temperature modification, are performed. A controlled interplay—that is to say, a state of mutual influence—between the body and the release of the gaseous and/or liquid media is thus achieved with the aid of the inventive device.

It should be noted here that lines are disposed at lateral or peripheral inlets and outlets of the applicator for feeding/filling the media into or releasing it from the chambers and/or channels, so that the body that is in contact with the applicator is not irritated by lines and/or inlets and outlets while the inventive device is in operating position.

In connection with the direct release of the chemical/physical parameters, for instance steam, it is also advantageous when at least one layer of the applicator, for instance the layer facing the body part, is permeable or semipermeable. This layer is preferably permeable on one side, so that the media can only move in one direction, namely out, but no substances can penetrate the chambers or channels. In the filling of—that is to say, the passage through—the chambers or channels, these gaseous or liquid media can reach the corresponding body parts through the permeable or semipermeable layer without hindrance. It is known that direct contact of the liquid and/or gaseous media (which contain therapeutic/comfort substances, for instance) with the skin of the body increases the effectiveness and the pleasure of a patient who is in contact with them. The permeability or semipermeability can be realized by means of various holes or pores of various types, for instance simple pores such as round pores, notches, intersecting notches, valves, simple permeable or semipermeable weaves or suchlike. Of course, a combination of pass mechanisms which guarantees unimpeded contact of the media with the body surface is likewise possible.

For optimal utilization of the inventive device, it is particularly advantageous when at least one layer of the applicator, preferably the layer that is averted from the body part, is impermeable to the substances in the chambers and/or channels. That way, the media in the chambers and/or channels are prevented from undesirably escaping from the layer that is farthest from the body or body parts, and the release of the substances occurs purposefully across the layer facing the body. At the same time, conduction of the media in the chambers and/or channels can be regulated more easily, because an escape of the substances is only permitted in one direction, namely across the openings of the side of the chambers/channels that faces the body.

Besides the release of the chemical/physical parameters across the chambers near the layer that faces the body part, advantage is also gained when at least one of the layers additionally comprises at least one channel that is fillable with gaseous and/or liquid media. These channels are likewise preferably disposed at the layer that faces the body and are permeable or semipermeable as in the above cited embodiment, so that the same or different substances can be additionally purposefully released directly onto the body surface via these channels. A regulatable release of liquid or gaseous media is thereby increased. Of course, the casing surrounding the channel can also be impermeable, so that, for instance, only a pressure delivery (pressure charge) can occur through the channels, whereby other combinations of the casings are also possible. It is also imaginable that these channels do not serve for exclusively for release but rather for draining residues of gaseous and/or liquid media. Such residues can easily collect between the applicator and the body during utilization of the inventive device, as a result of which an unobstructed and purposeful receiving of substances over the skin of the body is no longer guaranteed. In such a case, it is particularly advantageous when such residues are transported away via the channels by slight suction, for example.

For a more flexible construction of the inventive device, the channels are attached, preferably detachably, to the layer that faces the body part being treated, so that they can be variably configured at random according to the requirements of the body part. Said attachment can be provided by means of velcro, snaps, or other fastening mechanisms which create a non-permanent connection to a layer of the applicator.

Another advantageous embodiment of the inventive device is wherein the chambers of the applicator are subdivided into additional mutually communicating subchambers. This subdividing makes it possible to provide several chambers or subchambers, each of which can contain gaseous and/or liquid media with a different composition. It is imaginable that the chambers or subchambers are configured on top of one another, and that an additional layer for dividing the chambers, which is impermeable, extends between the chambers or subchambers. In this configuration, it is particularly effective when at least one chamber that faces the body serves solely for releasing the chemical/physical parameters, and at least one chamber that is averted from the body serves for fitting. Communication between the subdivisions can be realized by means of various openings such as valves or various types of pores (as mentioned above), these allow the media in the subdivisions/chambers to pass through more or less easily.

It is also advantageous when the channels are configured one inside another. This makes it possible to provide an inner channel within a channel, said channels being coaxial to one another. The channels can comprise a permeable or semipermeable or impermeable casing, depending on whether they are filled with gaseous and/or liquid media, it being important to prevent unwanted interaction between gas and liquid. On the other hand, it is possible for the inner channel to be separately filled with gases such as $O_2$, $CO_2$, or $O_3$, which penetrate through its permeable casing into the surrounding channel, which is filled with liquid, so that the liquid can be charged with gas during utilization of the inventive device. This type of utilization can also be realized by the juxtaposition of two or more inner channels which contain gaseous and/or liquid media of differing compositions and which supply the gaseous and/or liquid medium in the surrounding channel accordingly in order to then release it directly onto the body being treated. A juxtaposed configuration of the channels—i.e. the inner channels—is particularly expedient, because the media with different compositions can be released onto the skin surface of the body individually and in doses. For optimal control and precise adaptation to the requirements of the body or the patient that is wrapped or covered with the applicator, it is advantageous when the control device is connected to valves in lines for the gaseous and/or liquid media for regulating the flow volume of the gaseous and/or liquid media. This guarantees that a purposeful release of the media onto the body or body parts is achieved, namely in that the corresponding flow volume is increased by opening the valves in the lines, so that an increased volume or concentration of gaseous and/or liquid media can be released directly onto the body or body parts. It is also possible to supply different body locations with different media or media of different compositions or to subject them to different pressures.

It should be noted here that the inventive device, specifically the control device, can be manually controlled in case of a failure of the biosensors or the computer, so that adverse events can be avoided.

It should also be noted that the applicator is produced from a flexible material such as orientated polytetrafluoroethylene or PVC. Such a material guarantees an optimal fitting of the applicator to the body or body parts on which it is laid. Furthermore, such material is heat resistant and exhibits repellent properties with respect to oily substances and salts. In addition, it makes possible multiple re-use of the applicator, because this material is distinguished by its longevity and washability.

The applicator and, if so desired, the biosensors of the inventive device are advantageously disposed in a dimensionally stable casing that at least partially surrounds the body or body parts. This embodiment is particularly suitable for setting broken bones, it being possible to exert pressure on specific locations of the body or body parts in doses in a purposeful manner by pressure-charging individual chambers while bracing at the casing, whereby the influence of the pressure can be observed by x-ray monitoring, for example. Besides this, a massage effect can be achieved by periodically pressure-charging and then discharging certain cells, which effect can be enhanced by releasing various substances (gases, creams, therapeutic waters, aromas, scented oils, and suchlike) through the channels. The creams can also be spread on the body prior to the treatment, whereby the above described massage effect can be modified, for instance by the introduction of gasses (ozone, carbon dioxide, nitrogen). Therapeutic baths can also be realized with minimum amounts of therapeutic water. The applicator and the casing can also be realized as simple articles of clothing (overalls), whereby upward and downward movement can be generated by the pressure charging so that the body or body part can be carefully moved, for instance in underwater therapy. In the rehabilitation of paralyzed limbs, for instance, a simple, purposeful motion therapy including feedback by means of biosensors can be provided for the first time. The connecting lines between the applicator, the biosensors, and the control device can be constructed such that they can be easily disconnected or reliably interrupted.

It is also imaginable that the inventive applicator is attached as a lining in a tub, preferably by clamping. A clamping mechanism can be provided which allows the raising and lowering of the applicator in the tub, so that a body that is being treated can lie on the applicator and be lowered into the tub. Given utilization of the inventive device in this form, it is also imaginable that the tub itself can be filled with gaseous and/or liquid media, and these media themselves can exert a pressing force for fitting the applicator to the form of the body. Accordingly, the applicator can be utilized exclusively for emission, for instance the emission of pleasing vapors. Utilization of the inventive device in conjunction with a tub can be further enhanced by laying another therapeutic or comfort medium such as hay, mud, or the like, between the applicator and the body. Care should be taken here that the openings of the chambers or channels on the side that faces the body do not become clogged or mispositioned, so that unobstructed access and passage by the media in the chambers and/or channels is still allowed.

Other features which are considered as characteristic for the invention are set forth in the appended claims.

Although the invention is illustrated and described herein as embodied in a film-tub biocontrol, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIGS. 3A to 3E are several perspective views of channels of various constructions according to the invention.

DESCRIPTION OF THE PREFERRED EMBODIMENT

Figure 1:
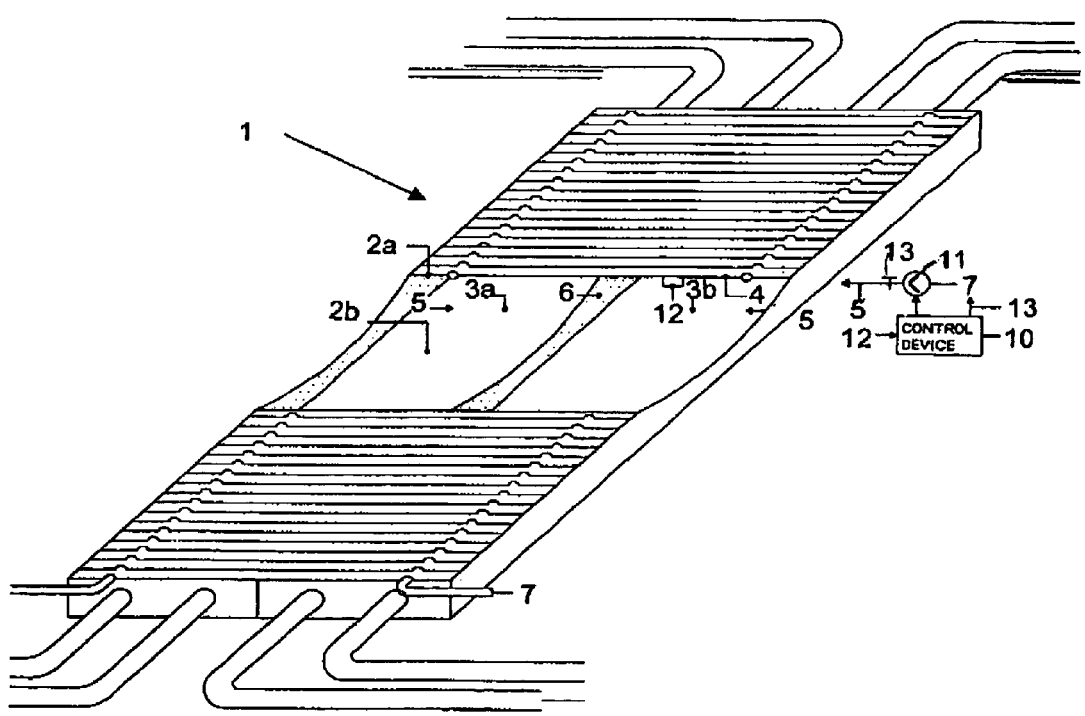
FIG. 1 is a perspective view of the inventive applicator with two chambers and a permeable or semipermeable layer that faces the body part.

Referring now to the figures of the drawing in detail and first, particularly, to FIG. 1 thereof, there is shown an applicator 1 according to the invention. The applicator 1 has two layers 2a, 2b as primarily important components, whereby the space between the layers 2a, 2b includes two chambers 3a, 3b, each of which is equipped with lines 5 peripherally, i.e. in the margin region. The layer 2a that faces the body (here the top layer) is permeable or semipermeable (openings 4), and the layer 2b that is averted from the body (here the bottom layer) is impermeable. In this simple exemplary embodiment of the present invention, the applicator 1 is laid on a body or parts thereof with its layer 2a that is provided with openings 4 coming in contact with the body surface. The layer 2b that is averted from the body serves as a shaping layer and exhibits insulating characteristics. Gaseous and/or liquid medium such as liquid that is charged with scents is poured into the chamber 3a peripherally via the lines 5. The pouring being performed and controlled by means of a control device 10. On their part, these two chambers 3a, 3b can communicate via one or more openings 6, so that the medium flowing into the chamber 3a can also penetrate the second chamber 3b. In the chamber 3a, the medium can be heated to its boiling point by means of non-illustrated filaments, for example, so that it reaches the chamber 3b via the opening 6 in a vapor state, whereby it is released onto the body surface (skin) from both chambers via the openings 4. After utilization, the medium is transported away via the peripheral line 5 of the chamber 3b.

Conduction in and out is usually achieved by means of pumps 11 of the control device 10. Depending on the requirements of the instance of application, the chambers 3a and 3b can also be filled individually via the lateral lines 5, whereby the opening 6 that connects the chambers 3a, 3b remains closed. In that case, the body location being treated can be supplied with two media of different compositions. Upon completion, the lines 5 also serve for draining the media from the respective chambers 3a, 3b.

As already mentioned in the introduction, the control device serves not only for filling the chambers 3a, 3b or channels (FIG. 2) but also for controlling the gaseous and/or liquid media. The control device is therefore equipped with a computer which stores a sequence grid (computer program) of a specific release scheme. For instance, a specific temperature curve of the media that are fed to the chambers/channels can be called up in order to generate temperature changes of the media based on minimum and maximum temperature data defined in the sequence grid. This information is routed to the devices of the control unit that are provided for temperature modification and converted there, so that the temperature of the media is controlled according to the predetermined temperature curve.

In another application, a stored and retrieved media release scheme is converted by means of the control unit, and the chambers/channels are filled or controlled accordingly. One or several biosensors 12 that are strategically placed in required vicinity of the body being treated or at designed contact points, for example, register various parameters of the corresponding body locations depending on what sensors are used, whereby a combination of different sensors for different parameters can also be utilized. For example, if the biosensors 12 register an elevated temperature at a specific body location to which they are connected, this value (12) is forwarded to the computer of the control device and compared to a value that is already stored in the retrieved sequence grid. If this does not correspond to a defined value in the grid, a correction is performed, and the temperature controller in the control unit changes its settings, which have been preset according to the sequence grid, and the temperature of the medium in the chamber 3a or 3b is modified according to the detected temperature, so that the relevant body location is supplied with the lower-temperature medium, thereby preventing local overheating of the skin there.

With regard to the pressure-charging or shaping, the chambers 3a, 3b in the applicator represented in FIG. 1 are filled with gasses or liquids in order to achieve an optimal fit of the applicator 1 to the body, whereby pressure data that are stored in the computer are also executed according to this exemplary embodiment as well. As soon as an excessive pressure load on a body location adjoining the chamber 3a is detected by the biosensors, the value is corrected by means of the computer, and the flow volume of the gas/liquid flowing through the chambers 3a is reduced by the control device, for instance by means of valves 13, thereby relieving the relevant body location.

Figure 2:
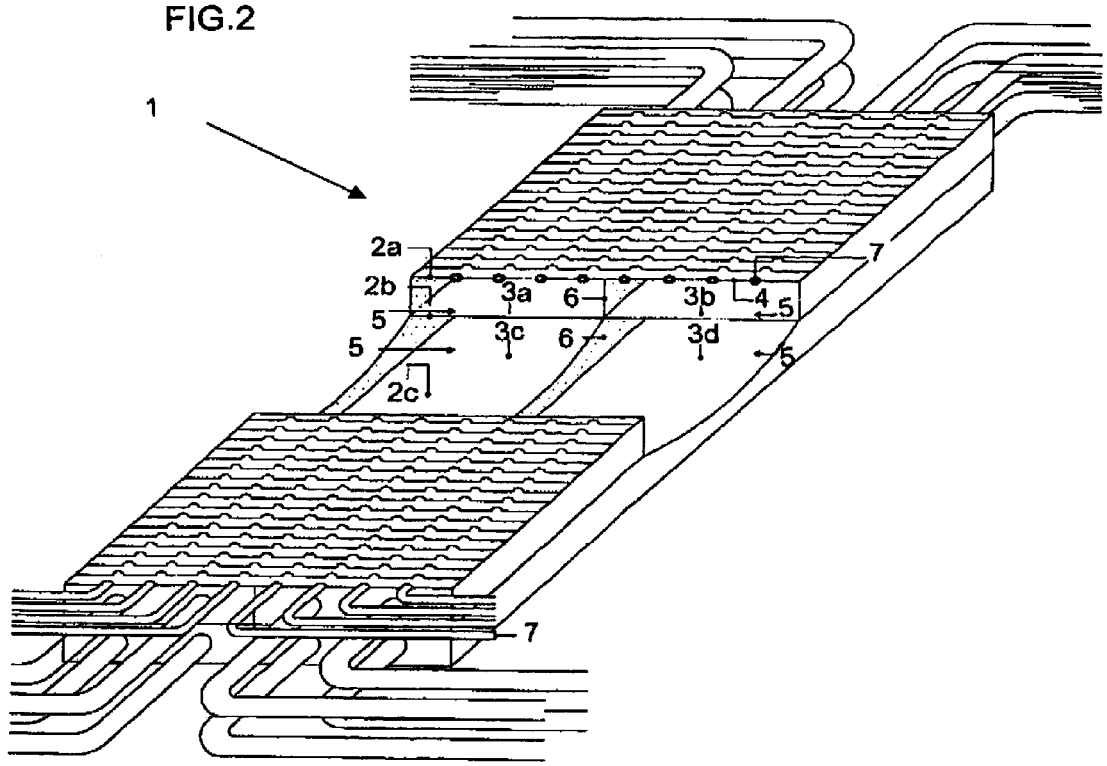
FIG. 2 is a perspective view of the inventive applicator with a subdividing of the chambers into four chambers and with channels at the layer that faces the body part.

FIG. 2 represents a more complex exemplary embodiment of the inventive device whereby the space between the layers 2a, 2b, 2c of the applicator 1 is subdivided into four chambers 3a, 3b, 3c, 3d, which are configured on top of one another and next to one another. The layer 2c that is farthest from the body (here the bottom layer) is impermeable (solid line); the intermediate layer 2b (here middle layer) is likewise impermeable; and the layer 2a that faces the body (top layer) is permeable or semipermeable. Lines 5 (in the margin or side region) supply the chambers 3a, 3b, 3c, 3d with liquid and/or gaseous media, whereby these, particularly the chambers 3a, 3b, can be exited again via openings 4 of the layer 2a. FIG. 2 further represents channels 7, namely two channels inside one another, which are disposed at the layer 2a that faces the body and which are detailed in FIG. 3. In FIG. 2 the channels 7 are configured at regular intervals, whereby an opening 4 is provided between each channel 7, and the channels extend transverse to the flowthrough direction of the gaseous or liquid media in the chambers 3a, 3b, 3c, 3d.

Given placement of the inventive applicator 1 on a body or body parts (not represented), the chambers 3a and 3b in FIG. 2 serve for the controlled release of liquid and/or gaseous media, whereas the chambers 3c, 3d that are averted from the body serve for fitting or pressure-charging. That is, greater or lesser amounts of gaseous or liquid medium are injected into chambers 3c, 3d, so that the chambers 3a, 3b contact the body securely and under controlled pressure. In this case, the chambers 3a, 3b serve solely for releasing the liquid or gaseous media, which is performed as explained in connection with FIG. 1, namely by the filling of the chambers 3a, 3b, 3c, 3d according to a routine scheme that is retrieved from the computer of the control device where it is stored, the detection of body parameters by means of the biosensors, and the corresponding regulating of the operations of the media in the chambers 3a, 3b, 3c, 3d by means of the control device. In this case, a pressure discharge can be effected in controllable fashion, for instance by way of one-way valves (not represented), the openings 4, or the laterally arranged outflow lines.

Like the chambers 3a, 3b, 3c, 3d, the channels 7 of the layer 2a (FIG. 2) are also individually fillable with liquid and/or gaseous media and individually controllable by means of the control device and the computer.

The channels 7 have permeable or semipermeable casings depending on the whether the channels 7 are utilized as release devices or solely for pressure charging (see FIG. 3). Their disposition at the layer 2a increases a local effect on body locations requiring specific treatment. For example, the concentration of the media flowing through the channels is increased and released only at the relevant body locations in controlled fashion depending on the values detected by the biosensors. The channels 7 can be separately utilized, so that different body locations which exhibit different reactions are supplied via the biosensors and accordingly via the control device.

The channels 7 can also be utilized as outflow lines for the media released by the chambers 3a, 3b, whereby there occurs not only circulation based on conduction in and out of the chambers 3a, 3b, 3c, 3d, but also an additional draining of the substances that are released by the chambers 3a, 3b via the channels 7.

FIG. 3 represents different shapes of channels 7 and different casings, whereby FIG. 3a represents openings 8 that are permeable one side for liquid or gaseous media. Here, liquids or gases can get out but cannot penetrate back into the channel 7. FIG. 3b represents openings 9 that are permeable on both sides for gaseous or liquid media, which are particularly suitable for transporting the excess media out of the environment of the channel 7. FIG. 3c represents two channels 7, 7a extending inside one another, which are disposed coaxial to one another and which include openings 8 that are permeable on one side for gasses and liquids. Here, the inner channel 7a can carry a gaseous medium while the surrounding channel 7 is passed by a liquid. The openings 8 of the inner channel 7a, based on their one-sided permeability, allow a charging of the liquid that is located in the surrounding channel 7 with the gas of the inner channel 7a, whereby it is impossible for the gas to be adversely influenced by the liquid. This liquid-gas mixture can be released onto the body via the openings 8 in the surrounding channel 7.

In FIG. 3d the channels 7 and 7a are again configured coaxial to one another, whereby the inner channel 7a contains a gaseous medium, and the surrounding channel 7 contains a liquid medium. The inner channel 7a which is filled with gas can additionally be utilized for pressure-charging, while at the same time a liquid medium can be released through the channel 7 that is provided with one-sided openings 8.

Figure 3E:
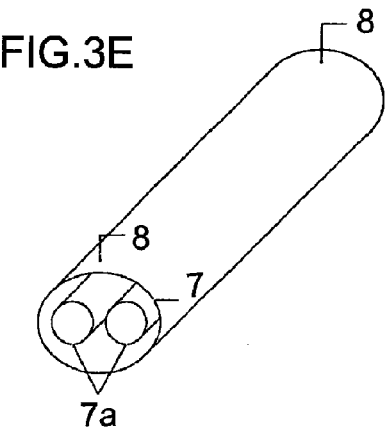

As represented in FIG. 3e, two or more inner channels 7a can be juxtaposed and led through a surrounding channel 7. The casings of the corresponding inner channels 7a and the surrounding channel 7 can be provided with combinations of openings of various permeability, so that desired mixtures of media can be formed as a result of the interaction between the individual media, and these mixtures can be conducted to the corresponding body location. In the present case, the channel 7 comprises openings 8 that are permeable on one side, while the inner channels 7a are constructed as in FIG. 3d.

In summary, based on the interplay of the biosensors and the control device that is connected to it, different media with different compositions, for instance different saturations, mix ratios, concentrations, pressures, temperatures, states of aggregation, and so on, can be effectively and easily adapted to the body depending on its response and can be released and purposefully conducted without obstruction to wherever a desired effect is wanted.

I claim:

1. A device for releasing chemical/physical parameters, the device comprising:
    a flexible applicator sized and configured to wrap and/or cover an entire body or body parts, said applicator being made of flexible material and having at least two layers defining a space therebetween with at least two closed chambers or channels laterally adjacent one another, each chamber or channel being independently and individually fillable with fluidic media for independently and individually releasing the chemical/physical parameters;
    one of said layers of said applicator being configured to face the body or body parts and being provided with openings for releasing liquid media directly to the body or body parts;
    a control device connected to said applicator for controlling functional parameters, including a flow volume, a temperature, and a pressure, of the medium in said space; and
    sensors connected to said control device, the media in the respective chambers or channels being controlled by said control device in dependence on the body parameters detected by said sensors.

2. The device according to claim 1, wherein said sensors are biosensors for detecting body parameters of a body adjoining said applicator.

3. The device according to claim 2, wherein said body parameters include a body temperature and an EKG output.

4. The device according to claim 1, wherein said chambers are connected via closable openings.

5. The device according to claim 1, wherein said chambers or channels are disposed in vicinity next to one another or below one another.

6. The device according to claim 1, wherein said at least one layer is formed with pores, valves, or semipermeable weaves.

7. The device according to claim 1, wherein at least one layer of said applicator is impermeable to the fluidic media in said chambers or channels.

8. The device according to claim 7, wherein said at least one layer is averted from the body part.

9. The device according to claim 1, wherein each of said chambers is subdivided into additional mutually communicating subchambers.

10. The device according to claim 1, wherein said control device is connected to valves in feed lines for said fluidic media, for controlling a flowthrough volume of the fluidic media.

11. The device according to claim 1, wherein said layers of said applicator are produced from a material selected from the group consisting of orientated polytetrafluoroethylene and polyvinylchloride.

12. The device according to claim 1, wherein said applicator is disposed in a dimensionally stable casing surrounding the body or body parts at least partially.

13. The device according to claim 12, wherein said sensors are disposed inside said stable casing.

14. The device according to claim 1, wherein at least one further channel is disposed at said layer of said applicator facing the body part.

15. The device according to claim 14, wherein said at least one further channel is fillable with gaseous and/or liquid media.

16. The device according to claim 14, wherein said at least one further channel is permeable or semi-permeable for releasing the gaseous and/or liquid media to the body or body parts.

17. The device according to claim 14, wherein said at least one further channel is formed with openings.

18. The device according to claim 17, wherein said openings are permeable on one side or said openings are permeable on both sides.

19. The device according to claim 14, wherein said at least one further channel is impermeable.

20. The device according to claim 14, wherein said at least one further channel is one of a plurality of channels detachably attached to a layer of said applicator.

21. The device according to claim 14, wherein said at least one channel is one of a plurality of channels extending one inside another.

22. A device for releasing chemical/physical parameters, the device comprising:

liquid media;

a flexible applicator sized and configured to wrap and/or cover an entire body or body parts, said applicator being made of flexible material and having at least two layers defining a space therebetween with at least two closed chambers or channels laterally adjacent one another, each chamber or channel being independently and individually fillable with said liquid media for independently and individually releasing the chemical/physical parameters;

one of said layers of said applicator being configured to face the body or body parts and being provided with openings for releasing said liquid media directly to the body or body parts;

a control device connected to said applicator for controlling functional parameters, including a flow volume, a temperature, and a pressure, of said liquid media in said space; and sensors connected to said control device, said liquid media in said respective chambers or channels being controlled by said control device in dependence on the body parameters detected by said sensors.

* * * * *